United States Patent [19]
Bauer et al.

[11] 4,318,985
[45] Mar. 9, 1982

[54] METHOD AND DEVICE FOR DETECTING GLUCOSE CONCENTRATION

[75] Inventors: Robert Bauer, Bristol; Myron C. Rapkin, Elkhart, both of Ind.

[73] Assignee: Miles Laboratories, Inc., Elkhart, Ind.

[21] Appl. No.: 229,733

[22] Filed: Jan. 29, 1981

[51] Int. Cl.³ .............. G01N 33/52; G01N 33/66
[52] U.S. Cl. .................. 435/14; 23/901; 422/56; 435/28; 435/805
[58] Field of Search .......... 435/14, 805, 28; 422/56; 23/901

[56] References Cited

U.S. PATENT DOCUMENTS

| | | | |
|---|---|---|---|
| 2,850,359 | 9/1958 | Worthington | 435/14 X |
| 3,092,465 | 6/1963 | Adams, Jr. | 435/14 |
| 3,123,443 | 3/1964 | Smeby | 435/14 |
| 3,350,278 | 10/1967 | Gretton | 435/14 |
| 3,598,704 | 8/1971 | Dahlqvist | 435/14 |
| 3,630,957 | 12/1971 | Rey | 435/14 X |
| 3,964,870 | 6/1976 | Tiedmann | 435/14 |
| 3,977,944 | 8/1976 | Muller-Matthesius | 435/14 |
| 4,148,611 | 4/1979 | Nand | 422/56 |
| 4,211,845 | 7/1980 | Genshaw | 422/56 |
| 4,254,220 | 3/1981 | Meiatini | 435/14 |
| 4,260,680 | 4/1981 | Muramatsu | 435/14 |
| 4,273,868 | 6/1981 | Walter | 435/14 |
| 4,279,993 | 7/1981 | Magers | 422/56 X |

FOREIGN PATENT DOCUMENTS

| | | | |
|---|---|---|---|
| DL135243 | 4/1979 | Fed. Rep. of Germany | 435/14 |
| WO80/01389 | 10/1980 | Int'l Appl. | 435/14 |
| 2004062 | 3/1979 | United Kingdom | 435/14 |

Primary Examiner—Sidney Marantz
Attorney, Agent, or Firm—James D. McNeil

[57] ABSTRACT

A method and test device for determining the glucose concentration in a test sample containing from ½ to 5 percent glucose. The method and test device involve incorporating urea-formaldehyde resin in a carrier matrix and subsequently impregnating the carrier with an enzymatic testing composition which includes glucose oxidase, a peroxidatively-active compound and a chromogen. Contact of the carrier with a glucose-containing test sample produces a detectable response whereby the glucose concentration can be determined.

10 Claims, 2 Drawing Figures

THE INFLUENCE OF UREA-FORMALDEHYDE (U-F) ON QUANTITATION OBTAINED WITH WHATMAN 3 MM PAPER

THE INFLUENCE OF UREA-FORMALDEHYDE (U-F) ON QUANTITATION OBTAINED WITH WHATMAN 3 MM PAPER

THE INFLUENCE OF UREA-FORMALDEHYDE (U-F) ON QUANTITATION OBTAINED WITH WHATMAN 31 ET PAPER

METHOD AND DEVICE FOR DETECTING GLUCOSE CONCENTRATION

BACKGROUND OF THE INVENTION

The detection of glucose in body fluids, as well as the determination of its concentration therein, is of great importance for diabetic patients who must control their diets so as to regulate their sugar intake and who must frequently be guided in this regard by a regular check on urine glucose. The determination of glucose in urine is also important where large numbers of people are screened to determine the incidence of diabetes among them.

Because early diagnosis and continued control are so important in diabetes, a sugar test, to be of greater value, must be conveniently rapid, simple enough for the technician or patient to learn with ease, accurate enough to serve the clinician or patient and sensitive enough to reflect variations in the patient's condition.

Currently there are available sophisticated biochemical systems which can be incorporated into dry, dip-and-read reagent strip devices, used in solution or suspension techniques, or in conjunction with spectrophotometics and other read-out systems.

These strips comprise a plastic strip, having at one end a carrier portion impregnated with an enzymatic testing composition which includes the enzyme glucose oxidase and a peroxidatively-active compound, e.g., peroxidase, or heme, and one or more indicator compounds as the principal active ingredients. Buffering agents may be present to keep the pH of the reactants at the site of reaction at a predetermined pH range. The strip utilizes an enzyme system wherein the glucose is a substrate for glucose oxidase. Glucose is oxidized to gluconic acid with the concomitant formation of hydrogen peroxide. Indicator compounds present undergo color changes in the presence of hydrogen peroxide and peroxidase. Various indicators can be used including "benzidine-type" chromogens, e.g., benzidine, o-tolidine and tetramethylbenzidine and substituted aniline chromogens. A combination of indicators can be utilized.

The glucose enzymatic test strips referred to above enable the assay of glucose levels by measuring the rate of color change which the indicator undergoes, i.e., by a rate reaction. The sample to be analyzed for glucose is contacted with the reagent-incorporated carrier portion by momentarily immersing the carrier portion into the sample or by applying an aliquot of the sample to the carrier portion and measuring the response after a set period of reaction time, by comparing any color formed in the carrier portion with a standard color chart calibrated to various glucose concentrations.

The general principles of chemical reaction kinetics apply to enzyme-catalyzed reactions, but enzyme-catalyzed reactions also show a distinctive feature not usually observed in nonenzymatic reactions, saturation with substrate. The rate equation for reactions catalyzed by enzymes having a single substrate, e.g., glucose, is expressed by an equation known as the Michaelis-Menten equation. Under certain reaction conditions, the Michaelis-Menten equation can be used to derive a value known as the Michaelis-Menten constant ($K_M$) [See *Biochemistry*, Lehninger, 2nd Edition, pp. 189–192]. The equation expresses the mathematical relationship between the initial rate of the enzymecatalyzed reaction and the concentration of the substrate.

At high substrate concentrations, the $K_M$ of the glucose oxidase is exceeded, and the reaction rate becomes nearly independent of concentration - this means that at such concentrations, it becomes difficult to determine concentrations of glucose based on a rate reaction color change. In the glucose-glucose oxidase system, as the level of glucose present approaches 2 percent, the $K_M$ of glucose oxidase is exceeded, rendering it difficult to determine with accuracy the glucose level of the sample being tested.

Since diabetic patients can have glucose levels of 50 mg/dl (0.05%) to 10,000 mg/dl (10%) and glucose levels of about ½ to 5 percent are not uncommon, it is important to be able to quantitatively determine glucose levels within this latter range. At present, dip-and-read reagent strips do not enable determination of glucose levels over a range of about ½ to 5 percent glucose.

The present invention provides a method of measuring glucose levels of about ½ to about 5 percent, using a dip-and-read reagent strip.

SUMMARY OF THE INVENTION

The present invention is directed to an enzymatic method for determining the glucose concentration in a test sample containing from about ½ to 5 percent glucose. The method involves first incorporating into a carrier portion of a test device from 0.005 percent to 2.5 percent by weight urea-formaldehyde resin and forming a cross-linked polymer.

The carrier is then impregnated with an enzymatic testing composition containing as the principal ingredients, glucose oxidase, a peroxidatively-active compound and a chromogen. The test sample is then contacted with the test device, a detectable response observed and the glucose concentration is determined. The device of the present invention comprises a carrier matrix treated with from 0.005 percent to 2.5 percent urea-formaldehyde resin and subsequently impregnated with an enzymatic testing composition containing glucose oxidase, a peroxidatively-active compound and a chromogen.

DESCRIPTION OF THE PREFERRED EMBODIMENT

Figure 1:
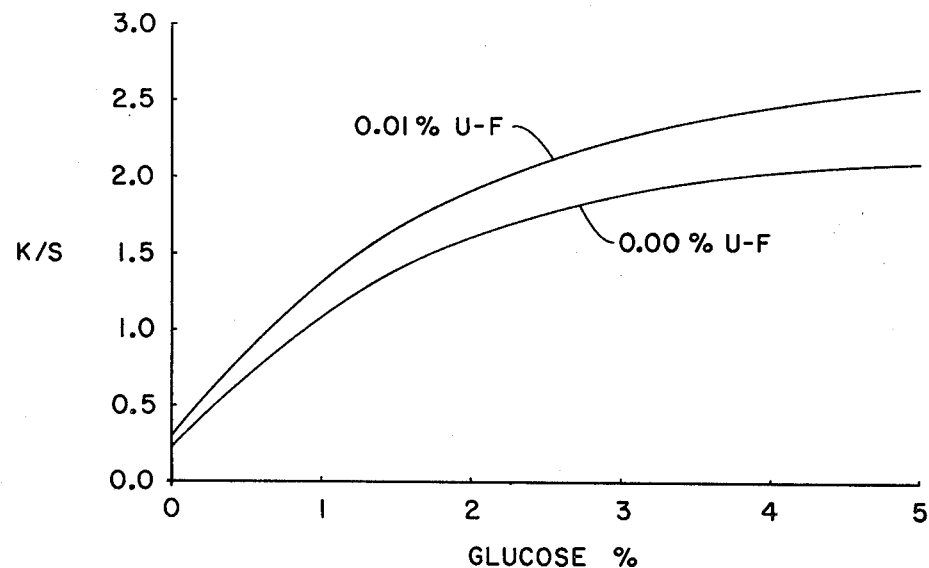

The carrier member used in the present invention can take on a multitude of forms. It can be mono- or multiphasic, comprising one or more appropriate materials or mediums of similar or different absorptive or other physical characteristics. It can be hydrophobic or hydrophilic, bibulous or nonporous. It can take on many known forms such as those utilized for enzymatic reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper carrier element. French Pat. No. 2,170,397 teaches the use of carrier members having greater than 50 percent polyamide fibers therein. Another approach to carrier members is disclosed in U.S. Pat. No. 4,046,513 wherein the concept of printing reagents onto a suitable carrier is employed. U.S. Pat. No. 4,046,514 discloses the interweaving or carrier member being dipped sequentially into each with drying steps between dippings. In such a case a porous material such as paper might be most advantageous. Alternatively, it might be desirable to utilize a multiphasic carrier member, where two or more layers of porous material are affixed one atop another. Still another approach to carrier member incorporation is to sequentially coat a continuous polymer with coatings containing different reagents of the immunoassay system. Filtering layers can be present in the carrier member to preclude potential interfering agents from reaching the assay system, while permitting access to any analyte present in the sample.

Prior to impregnating the carrier portion with the enzymatic testing composition, the carrier portion is first treated with urea-formaldehyde. The range of urea-formaldehyde which produces improved determination of glucose levels is from about 0.005 percent to 2.5 percent by weight. A preferred urea-formaldehyde concentration is about 0.01 percent by weight. Using equal amounts by weight of urea and formaldehyde provides a 1:2 urea:formaldehyde molar ratio.

If the matrix is paper the paper can be impregnated with a urea-formaldehyde resin, or alternatively, commercially available paper, containing urea-formaldehyde, can be used.

During commercial paper-making operations, urea-formaldehyde resins can be added in the initial stage, by mixing the resin into the "beater". Examples of commercially available urea-formaldehyde papers containing from 0.005 to 2.5 percent by weight urea-formaldehyde, suitable for use in the present invention are: Mead 624, manufactured by the Mead Corporation, Schillen Park, Ill. 60176; FW-9, S-10 or B-22 paper, manufactured by the Buckeye Cellulose Corporation, Memphis, Tenn. 38108; and Grade 250, manufactured by Eaton-Dikeman Co., Mount Holly Springs, PA 17065.

The reaction between urea and formaldehyde is well known; the components react to form dimethylol urea at nearly 100 percent yield. As the matrix is aged for several days, condensation reactions occur which result in a cross-linked urea-formaldehyde polymer. Alternatively, the rate of cross-linking can be increased by subjecting the urea-formaldehyde treated matrix to heat. Following formation of the cross-linked polymer, the paper is then ready for treatment with the enzymatic testing composition as indicated below.

As indicated earlier, the carrier portion has incorporated therein glucose oxidase, a peroxidatively-active compound, e.g., peroxidase or heme, and an indicator, e.g., a "benzidine-type" chromogen or substituted aniline chromogen or a combination thereof. In addition, one or more water soluble polymers may be incorporated, e.g., polyvinyl pyrrolidine and a surfactant, e.g., a polyethoxylated fatty alcohol, such as ON870, available from GAF, New York, N.Y., to provide more uniform color during glucose testing.

The carrier matrix can be impregnated with the enzymatic testing composition in several ways known to a person of reasonable skill in the art. One way is to pass a web of the carrier matrix material through an impregnating bath containing the testing composition ingredients so that the matrix becomes thoroughly saturated with impregnating solution. The saturated matrix is then dried, as in an air oven at 50° C., leaving the test composition incorporated within the matrix. As described in the following examples, another way involves dipping the carrier into the enzymatic testing composition and removing and drying the impregnated carrier.

EXAMPLE 1

A reagent solution was prepared containing 0.005 percent by weight urea and 0.005 percent by weight formaldehyde (1:2 molar ratio) in water. Strips of commercially available Whatman 3MM filter paper were dipped into this solution and dried for 15 minutes at 100° C. The treated paper strips were stored for 8 days at room temperature. Depending on the extent of the condensation reaction (loss of water), the amount of the urea-formaldehyde resin present in the resulting treated paper will be about 0.01 percent by weight.

The treated paper was then impregnated with a enzymatic testing composition having the following composition.

| | |
|---|---|
| Citrate buffer, 1.0M, pH 5.5 | 2.0 ml |
| Horseradish Peroxidase, 50 milligram/milliliter (mg/ml) | 2.0 ml |
| Glucose oxidase, 5000 U/ml | 3.0 ml |
| Polyvinyl pyrrolidine, 15% in ethanol | 1.9 ml |
| GAF ON870, 10% | 0.5 ml |
| m-anisidine | 0.112 ml |
| tetramethylbenzidine, 0.05M in ethanol | 0.5 |

The impregnated paper strips were dried at 60° C. for 15 minutes. Test strips prepared from these papers were dipped into urine which contained glucose concentrations ranging from 0.0 to 5 percent. Control sample strips were prepared by impregnating untreated Whatman 3MM filter paper with the above enzymatic testing composition.

The performance of the test strips prepared as described above was analyzed instrumentally using a device known as the "Rapid Scanner". This device is a scanning reflectance spectrophotometer interfaced with a PDP-12 computer obtained from the Digital Equipment Corporation. The instrument is used for the rapid measurement of reflectance spectra in the visual range. The computer allows for the storage of spectral data and computations. Measurements of the performances of test strips in the Rapid Scanner have the following advantages over visual observations.

1. The light source and conditions surrounding the sample remains fixed. In visual readings the light source can vary, not only in wavelength components, but also in relations to the locations of the strips being observed.

2. The detector characteristics remain fixed in the Rapid Scanner. In visual observation, the detector (i.e. in the eyes of the observer) varies from person to person and, with the same person, from day to day.

3. The Rapid Scanner allows more precise quantitation of the data than does human observation, thereby permitting comparisons between the results to be made in a more objective manner than with visual observation.

The Rapid Scanner instrument was constructed by the Ames Division of Miles Laboratories, Inc., Elkhart, Ind., United States, from whom complete information with respect to structural and performance characteristics are obtainable.

Reflectance values obtained at 660 nanometers (nm) wavelength, after a 90 second interval, are represented graphically in FIG. 1; where K/S is plotted against glucose concentration. K/S is defined as follows:

$$\frac{K}{S} = \frac{(1-R)^2}{2R}$$

in which K is a constant, S is the scattering coefficient of the particular reflecting medium, and R is the fraction of reflectance from the test strip. This relationship is a simplified form of the well-known Kubelka-Munk equation [Gustav Kortüm, "Reflectance Spectroscopy", pp. 106–111, Springer-Verlaz, New York (1969)].

Slopes of segments of the K/S vs. percent glucose values of FIG. 1 were calculated, assuming linearity for the segments. The slopes obtained are shown in Table 1 below.

TABLE 1

| | K/S vs. Glucose Slope Values | | |
|---|---|---|---|
| Glucose (%) | With Urea-Formaldehyde | Without Urea-Formaldehyde | Percent $\left(\frac{without}{with}\right) \times 100$* |
| 0.0–0.5 | 1.18 | 1.04 | 88 |
| 0.5–1.0 | 0.76 | 0.70 | 92 |
| 1.0–2.0 | 0.67 | 0.56 | 84 |
| 2.0–5.0 | 0.20 | 0.16 | 80 |

*Based on "normalizing" the urea-formaldehyde slope as 100.

As seen in FIG. 1 and as calculated in Table 1, at glucose concentrations ranging from about ½ to about 5 percent, the urea-formaldehyde treated test strips have a greater slope than the untreated test strips. This greater slope indicates that in this glucose concentration range the reaction rate of the color change which occurs on the urea-formaldehyde treated carrier is still dependent upon the glucose concentration.

The numbers in the last column of Table 1 are based on assigning a "normalized" value of 100 to urea-formaldehyde impregnated papers. The numbers obtained indicate the lesser slope, and therefore lesser quantitation obtained, without the presence of urea-formaldehyde.

The untreated test strips have a lesser slope, i.e., are becoming more asymptotic at a faster rate in the range of about ½ to about 5 percent glucose concentration, indicating that the reaction rate of the color change which occurs on the untreated carrier is becoming more independent of glucose concentration, making it difficult to determine glucose concentration in a test sample within the range ½ to about 5 percent glucose.

EXAMPLE 2

A second series of test strips was prepared, using commercially available Whatman 31 ET filter paper, treating the paper strips with urea-formaldehyde and subsequently impregnating the paper with the enzymatic testing composition as described in Example 1.

Figure 2:
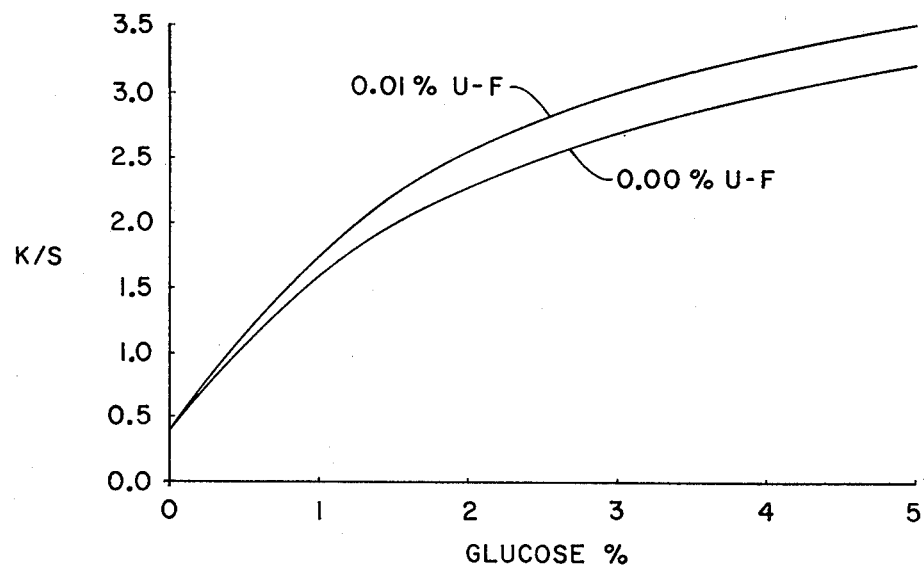

Reflectance values obtained at 660 nm, after a 90 second interval, are represented graphically in FIG. 2. K/S values were plotted against glucose concentration, and the slope of segments calculated, as summarized in Table 2 below.

TABLE 2

| | K/S vs. Glucose Slope Value | | |
|---|---|---|---|
| Glucose (%) | With Urea-Formaldehyde | Without Urea-Formaldehyde | Percent $\left(\frac{without}{with}\right) \times 100$ |
| 0.0–0.5 | 1.46 | 1.38 | 94 |
| 0.5–1.0 | 1.14 | 0.90 | 79 |
| 1.0–2.0 | 0.80 | 0.71 | 89 |
| 2.0–5.0 | 0.33 | 0.31 | 94 |

The results shown in FIG. 2 and Table 2 indicate that at glucose concentrations ranging from about ½ to 5 percent, the urea-formaldehyde treated test strips have a greater slope than the untreated test strips, indicating that the method and device of the present invention enables improved quantitation of the glucose concentration within this range.

What is claimed is:

1. In a test device for detecting the presence of glucose in a test sample, wherein said device comprises a carrier matrix incorporated with glucose oxidase, a peroxidatively-active compound and a chromogen, the improvement wherein the carrier matrix is incorporated with from 0.005 percent to 2.5 percent by weight urea-formaldehyde resin wherein there is formed a cross-linked polymer.

2. A test device as claimed in claim 1 wherein said carrier matrix is paper.

3. A test device as claimed in claim 1 wherein the urea-formaldehyde is present in an amount of about 0.01 percent by weight.

4. A test device as claimed in claim 1 wherein the chromogen is a benzidine-type indicator or a substituted aniline indicator and the peroxidatively-active compound is peroxidase.

5. A method for determining the glucose concentration in a test sample containing from about ½ to 5 percent glucose which comprises contacting said test sample with the test device of claim 1.

6. A method for determining the glucose concentration in a test sample containing from about ½ to 5 percent glucose which comprises contacting said test sample with the test device of claim 2.

7. A method for determining the glucose concentration in a test sample containing from about ½ to 5 percent glucose which comprises contacting said test sample with the test device of claim 3.

8. A method for determining the glucose concentration in a test sample containing from about ½ to 5 percent glucose which comprises contacting said test sample with the test device of claim 4.

9. A method for preparing the test device of claim 1 which comprises the steps of impregnating a carrier with 0.005 percent to 2.5 percent by weight urea-formaldehyde resin wherein there is formed a cross-linked polymer and subsequently impregnating the carrier with a composition effective to determine the presence of from ½ to 5 percent glucose in a test sample.

10. In a method for preparing a test device for the determination of glucose which includes contacting a carrier with a composition effective to determine said glucose, the improvement wherein said carrier is incorporated with from 0.005 to 2.5 percent by weight urea-formaldehyde resin wherein there is formed a cross-linked polymer.

* * * * *